United States Patent [19]

Okamoto et al.

[11] Patent Number: 5,693,255
[45] Date of Patent: Dec. 2, 1997

[54] OIL-IN-WATER TYPE EMULSION COMPOSITION

[75] Inventors: Toru Okamoto; Satoshi Tomomasa; Hiroyuki Kakoki; Shoji Nishiyama; Hideo Nakajima, all of Yokohama, Japan

[73] Assignee: Shiseido Co., Ltd., Tokyo, Japan

[21] Appl. No.: 213,023

[22] Filed: Mar. 15, 1994

[51] Int. Cl.$^6$ .................................................. B01J 13/00

[52] U.S. Cl. ................ 252/312; 252/314; 252/315.4; 514/846; 514/943; 514/944

[58] Field of Search .................... 252/312, 314, 252/315.2, 315.4; 574/846, 943, 944

[56] References Cited

U.S. PATENT DOCUMENTS

| | | |
|---|---|---|
| 3,341,465 | 9/1967 | Kaufman et al. . |
| 3,829,563 | 8/1974 | Barry et al. . |
| 3,917,830 | 11/1975 | Davis et al. ............................ 514/171 |
| 4,093,581 | 6/1978 | Anderson ................................ 524/747 |
| 4,380,503 | 4/1983 | Koerner et al. ......................... 252/314 |
| 4,595,586 | 6/1986 | Flom ........................................ 424/59 |
| 4,620,878 | 11/1986 | Gee ...................................... 252/312 X |
| 4,690,775 | 9/1987 | Schott et al. ............................ 252/312 |
| 4,702,916 | 10/1987 | Geria ...................................... 424/400 |
| 4,818,751 | 4/1989 | Ibe ............................................ 514/54 |
| 4,950,468 | 8/1990 | Nakamura et al. ................... 424/70.12 |
| 4,980,038 | 12/1990 | Watanabe et al. .................. 204/157.15 |

FOREIGN PATENT DOCUMENTS

| | | |
|---|---|---|
| A0472184 | 2/1992 | European Pat. Off. . |
| A0512270 | 11/1992 | European Pat. Off. . |
| A0538762 | 4/1993 | European Pat. Off. . |
| A2517985 | 6/1983 | France . |
| A2066659 | 7/1981 | United Kingdom . |
| A2165467 | 4/1986 | United Kingdom . |

OTHER PUBLICATIONS

Journal of Collid and Interface Science, vol. 28, 1986, pp. 82–91, "The Self Bodying Action Of The Mixed Emulsifier Sodium Dodecyl Sulfate/Cetyle Alcohol"; B.W. Barry.

*Primary Examiner*—Richard D. Lovering
*Attorney, Agent, or Firm*—Townsend & Banta

[57] ABSTRACT

An oil-in-water type emulsion composition comprising: an amphiphile and a surfactant selected from the substances which can form a gel in an amphiphatic substance-surfactant-water system at a temperature of not lower than ordinary temperatures; oil and water, wherein substantially the total amount of amphiphile and surfactant exist on the boundary surfaces of emulsion particles. The emulsion composition has both the physical properties close to those of an aqueous solution and a creamy feel at the time of use.

5 Claims, 3 Drawing Sheets

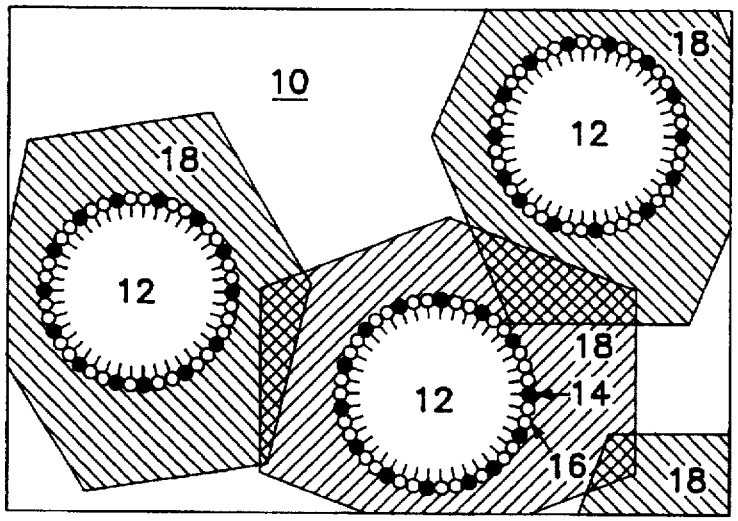
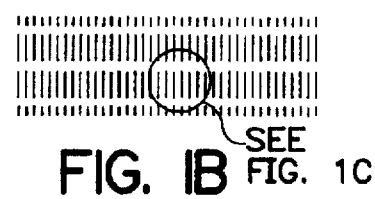
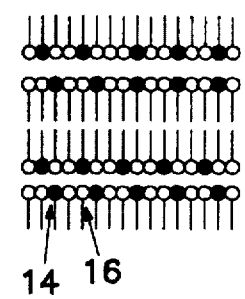
FIG. 1A
FIG. 1B
FIG. 1C
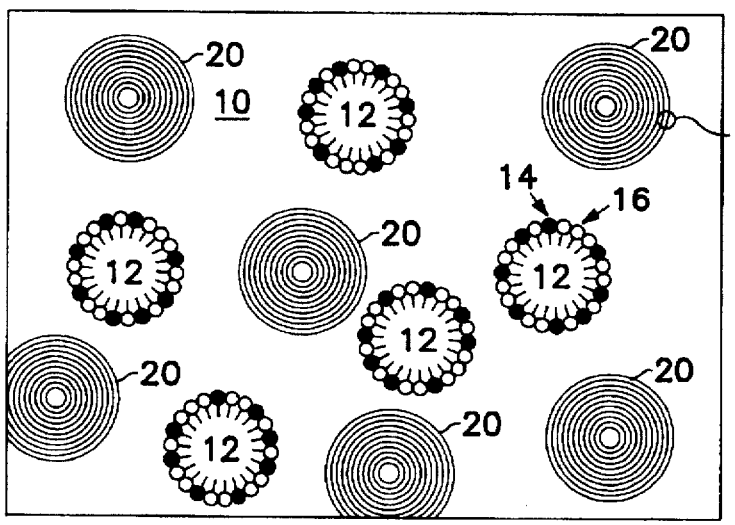
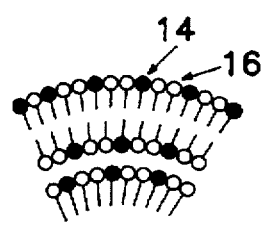
FIG. 2A
FIG. 2B

OIL-IN-WATER TYPE EMULSION COMPOSITION

FIELD OF THE INVENTION

The present invention relates to an oil-in-water type emulsion composition and, more particularly, to an improvement of the physical properties of an oil-in-water type emulsion composition.

BACKGROUND OF THE INVENTION

Various emulsion compositions are generally used in the field of cosmetics and the like.

Most of these emulsion compositions are creamy or milky, and emulsion compositions with the emulsion particle diameter reduced in order to improve the external appearance have been developed (e.g., Japanese Patent Laid-Open Nos. Sho 63-126542 (1988) and Hei 1-288330 (1989)). These emulsion compositions attract attention as a compound having an oily component stably mixed with the system without using a large amount of surfactant, ethanol, or the like.

Although these conventional emulsion compositions are excellent in stability and the transparency, various studies have been further undertaken so as to provide a more excellent feel, etc. at the time of use.

More specifically, it is desirable that an emulsion composition for a cosmetic have physical properties close to those of an aqueous solution in the container because it provides an excellent transparent external appearance, and the low viscosity improves the convenience at the time of packing or removed from the container. On the other hand, when the emulsion composition is applied to the skin, it preferably has a soft feel like cream.

However, no emulsion composition having such antipodal physical properties has been produced in the related art.

SUMMARY OF THE INVENTION

Accordingly, it is an object of the present invention to eliminate the above-described problems in the related art and to provide an oil-in-water type emulsion composition having not only the physical properties close to those of an aqueous solution, but also a creamy feel at the time of use.

As a result of studies undertaken by the present inventors so as to achieve this aim, it has been found that an oil-in-water type emulsion composition having substantially the total amount of amphiphile and surfactant which can form a gel in a water phase on each boundary surface between an oil phase as the inner phase and a water phase as the outer phase has not only physical properties close to those of an aqueous solution, but also a creamy feel at the time of use. On the basis of this finding, the present invention has been achieved.

In general, in oil-in-water type emulsions, it is considered that an amphiphile and a surfactant form gels in a water phase and solidify the base material(Barry, B. W., J. Colloid Interface Sci., 28, 82–91 (1968), etc.). A creamy feel of such an emulsion composition at the time of use is derived from the fluidity of the gels formed in a water phase by the amphiphile and the surfactant.

The formation of an gel in a oil-in-water type emulsion composition is described as follows on p. 112 to 116 of "Chemicophysics of Cetyl Alcohol" by Shoji Fukushima, published by Fragrance Journal (1992).

In FIG. 1, herein oil phase 12 is dispersed in a water phase 10, and a surfactant 14 and an amphiphile 16 exist on each boundary surface between the water phase 10 and the oil phase 12 so as to stabilize the dispersion of the oil phase 12 in the water phase 10.

The surfactant 14 and amphiphile 16 also exist in the water phase 10 and a part thereof forms lamella structures 18. The gel structures thus produced not only solidify the base material but also provide an excellent creamy feel at the time of use.

If the gel structures which solidify the base material in such an oil-in-water type emulsion composition are broken by an emulsifier having a strong shear force so that the lamella structure 18 is separated into fine dispersion systems (vesicles) 20, for example, as shown in FIG. 2, it is possible to obtain a liquid base material having a low viscosity (Michihiro Yamaguchi, Akira Noda, "Japan Chemis try" 26–32 (1989)). However, the system produced by finely dispersing the lamella structures suffers from a problems such as the generation of blobs due to agglomeration, and instability of the system such as an increase in the viscosity due to the reconstruction of the gel structure.

The present inventors have succeeded in producing a liquid cream having a low viscosity and assuring the stability of the liquid cream as an article of commerce by finely dividing the emulsion particles of an oil-in-water type emulsion composition which is composed of the amphiphiles 16, the surfactants 14, the water 10 and the oil 12, transferring the amphiphile 16 and surfactant 14 which form gels in the water phase 10 to the boundary surface of each emulsion particle so as to reduce the amount of gel in the water phase. This is accomplished by selecting a particular combination of the amphiphile 16 and the surfactant 14 which constitutes the stable gel, and which is difficult to reconstruct as a gel structure after the stable gel structure is broken.

When approximately the total amount of amphiphile 16 and surfactant 14 are transferred to the boundary surface of the oil drops 12, as shown in FIG. 3, the amphiphile 16 and the surfactant 14 are held stably on the boundary surfaces of the emulsion particles. Since finely dispersed lamella structures or the like do not exist in the water phase 10 of the present invention, there is no generation of blobs due to agglomeration, or reconstruction of the gel structure. Therefore, the oil-in-water type emulsion composition of the present invention has a very low viscosity in the preserved state, an excellent producibility, and is easy to remove from the container.

On the other hand, when the emulsion composition shown in FIG. 3 is applied to the skin, for example, the emulsion particles are mechanically broken by the spreading operation, so that the area of the boundary surface of each emulsion particle is greatly reduced. As a result, the amphiphile 16 and the surfactant 14 are discharged and transferred into water phase 10, and gel structures are reconstructed by amphiphile 16, surfactant 14 and water 10, thereby providing a composition which has a stable creamy feel to the skin.

In this way, the present inventors have developed an oil-in-water type emulsion composition, the emulsion of broken in the process of application, and which provides a novel creamy feel when it is applied to the skin.

In a first aspect of the present invention, there is provided an oil-in-water type emulsion composition comprising: (1) an amphiphile and a surfactant selected from substances which can form a gel in an amphiphile-surfactant-water system at a temperature of not lower than ordinary temperatures; (2) oil and (3) water, wherein substantially the total amount of amphiphile and surfactant exist on the boundary surface of emulsion particles.

In an oil-in-water type emulsion composition provided in a second aspect of the present invention, the amount of amphiphile and surfactant on the boundary surface is not less than 90% by area ratio according to DSC.

In an oil-in-water type emulsion composition provided in a third aspect of the present invention, the amphiphile and surfactant are selected from substances which can form a gel having a transition temperature not lower than 60° C. in the amphiphile-surfactant-water system.

In an oil-in-water type emulsion composition provided in a fourth aspect of the present invention, the emulsion particle diameter is not more than 0.15 µm.

In an oil-in-water type emulsion composition provided in a fifth aspect of the present invention, the amount of oil is not less than ½ of the total amount of amphiphile and surfactant.

In an oil-in-water type emulsion composition provided in a sixth aspect of the present invention, the total amount of amphiphile and surfactant is not less than 0.2 wt % of the water phase.

In an oil-in-water type emulsion composition provided in a seventh aspect of the present invention, the amphiphile is a higher alcohol and/or a higher fatty acid having a carbon chain length of not less than 16.

In an oil-in-water type emulsion composition provided in an eighth aspect of the present invention, the surfactant is a cationic surfactant or an anionic surfactant.

The structure of the present invention will be explained in more detail hereinafter.

It is necessary that the amphiphile and surfactant which are transferred to the boundary surface between the water phase and the oil phase, and which are characteristic of the present invention, specifically form a gel in an amphiphile-surfactant-water system. From the point of view of emulsion stability, the gel is preferably of the α-type, and it is more preferable that the transition temperature of the gel is not lower than 60° C. If a gel has a single peak of 21.4° by X-ray analysis, the gel is judged to be the α-type.

Examples of preferred combinations of amphiphiles and surfactants which form a gel in a water system at a temperature not lower than ordinary temperatures are behenic acid and/or behenyl alcohol (amphiphile)-potassium behenate (surfactant), stearic acid and/or stearyl alcohol (amphiphile)-potassium stearate (surfactant), stearyl alcohol (amphiphile)-sodium cetyl sulfate (surfactant), behenyl alcohol (amphiphile)-behenyltrimethyl ammonium chloride (surfactant) and behenyl alcohol (amphiphile)-stearyltrimethyl ammonium chloride (surfactant). It is possible to further enhance the emulsion stability by using a combination of an amphiphile and surfactant which have long and different carbon chain lengths.

Although the amphiphile has surface activity, the amphiphile itself has a strong hydrophobic property and the surface activity thereof is not as strong as a general surfactant. Examples of an amphiphile are higher fatty acids, higher aliphatic alcohols, monoglycerides, glycerol monoalkyl ethers, monoalkylamines, and compounds (cholesterol, phytosterol, etc.) having a sterol skeleton.

The amount of the oil phase is not less than ½, preferably, equal to the total amount of amphiphile and surfactant in the composition.

When the amount of oil phase is less than ½ of the total amount of amphiphile and surfactant, the emulsion stability with time is apt to decrease over time.

The average emulsion particle diameter is not more than 0.15 µm, preferably not more than 0.10 µm.

If the average emulsion particle diameter exceeds 0.15 µm, undesirable creaming may occur when the emulsion has a low viscosity. The average particle diameter of the emulsion used in the present invention have been measured by a dynamic light scattering method using NICOMF-270 (produced by HIAC/ROYCO).

It is considered that the water phase is gelated when an oil-in-water type emulsion composition of the present invention is spread over the skin. For this reason, if the total amount of amphiphile and surfactant is less than 0.2% of the amount of water phase, the gelation does not occur consequently in such compositions a creamy feel may not be obtained when the composition is spread on the skin.

The amount of amphiphile-surfactant for forming a gel in a water phase, i.e., 0.2% is generally small. However, since part of the water content evaporates and disperses when such an oil-in-water type emulsion composition is spread over the skin, about 0.2% of amphiphile and surfactant based on the amount of water phase can produce a creamy feel at the time of use. In a preferred composition, the amount of amphiphile and surfactant is not less than 0.5% of the amount of the water phase.

In the present invention, the oily component mixed in the system may be liquid oils, solid oils, semisolid oils and slightly water-soluble substances. For example, the oily component may be selected from liquid oils such as avocado oil, tsubaki oil, turtle oil, macadamia nut oil, corn oil, mink oil, olive oil, rape seed oil, yolk oil, sesame oil, persic oil, wheat germ oil, sazanque oil, castor oil, linseed oil, safflower oil, cottonseed oil, evening primrose oil, perilia oil, soybean oil, peanut oil, teaseed oil, kaya oil, rice bran oil, Chinese paulownia oil, Japanese paulownia oil, jojoba oil, germ oil, triglycerin, glycerin trioctanoate and glycerin triisopalmitate; solid oils such as cocoa butter, coconut oil, horseflesh tallow, hydrogenated coconut oil, palm oil, beef tallow, mutton tallow, hydrogenated beef tallow, palm kernel oil, pork tallow, beef bone tallow, Japan wax and hydrogenated castor oil; waxes such as bees wax, candelilla wax, cotton wax, carnauba wax, bayberry wax, Chinese wax, spermaceti wax, montan wax, rice bran wax, lanolin, kapok oil, lanolin acetate, liquid lanolin, sugarcane wax, lanolin fatty acid isopropyl, hexyl laurate, reduced lanolin, jojoba wax, hydrogenated lanolin, shellac wax, POE lanolin alcohol ether, POE lanolin alcoholacetate, lanolin fatty acid polyethylene glycol and POE hydrogenated lanolin alcohol ether; hydrocarbons such as liquid paraffin, ozocerite, squalene, pristane, paraffin, ceresin, squalane, vaseline and microcrystalline wax; synthetic esters such as isopropyl myristate, cetyl octoate, octyldodecyl myristate, isopropyl palmitate, butyl stearate, hexyl laurate, myristyl myristate, decyl oleate, hexyldecyl dimethyloctoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkl glycol monoisostearate, neopentyl glycol dicaprate, diisostearyl malate, glycerin di-2-heptylundecandate, trimethylolpropane tri-2-ethylhexylate, trimethylolpropane triisostearate, pentaerythritol tetra-2-ethylhexylate, glycerin tri-2-ethylhexylate, cetyl-2-ethylhexandate, 2-ethylhexyl palmitate, glycerin trimyristearate, glyceride tri-2-undecandate, castor oil fatty acid methyl ester, oil oleate, cetostearyl alcohol, acetoglyceride, 2-heptylundecyl palmitate, diisopropyl adipate, N-lauroyl-L-glutamic acid-2-octyldodecyl ester, di-2-heptylundecyl adipate, ethyl laurate, di-2-ethylhexyl cebacate, 2-hexyldecyl myristate, 2-hexyldecyl palmitate, 2-hexyldecyl adipate, diisopropyl cebacate, 2-ethylhexyl succinate, ethyl acetate, burylacerate, amyl acetate and triethyl citrate; higher fatty acids such as lauric acid, myristic acid, palmitic acid, stearic acid, behenic acid, oleic acid, 12-hydroxystearic acid, undecylenic acid, Tall acid, lanolin fatty acid, isostearic acid, linoleic acid, linolenic acid and eicosapentaenoic acid; straight-chain or branched higher alcohols such as laurin alcohol, cetyl alcohol, stearyl alcohol, behenyl alcohol, myricyl alcohol, cetostearyl alcohol, monostearyl glycerin ether (batyl alcohol), 2-decyltetradecynol, lanolin alcohol, cholesterol, hexyldodecanol, isostearyl alcohol and octyldodecanol; chained polysiloxanes such as dimethyl polysiloxane, methylphenyl polysiloxane, methylhydrogen polysiloxane; Cyclic polysiloxanes such as octamethylcyclotetrasiloxane, decamethylcyclopentasiloxane, dodecamethylcyclohexasiloxane, tetramethyltetrahydrogen-cyclotetrasiloxane; amino denatured silicone oil, epoxy denatured silicone oil, epoxy polyether denatured silicone oil, polyether denatured silicone oil, carboxy denatured silicone oil, alcohol denatured silicone oil, alkyl denatured silicone oil, ammonium salt denatured silicone oil, silicone resin which has a network structure or can form the network structure such as trimethylsiloxy cinnamate; silicone rubber such as highly polymerized dimethyl polysiloxane, highly polymerized methylphenylsiloxane, highly polymerized methyl vinyl polysiloxane; perfluorocarbon such as perfluoro decaline, perfluorohexane, triperfluoro-n-butylamine; perfluoropolyether; vitamins such as vitamin A and derivatives thereof; vitamin D and derivatives thereof, vitamin E and derivatives thereof, vitamin K and derivatives thereof; sterols; and natural and synthetic perfumes. The oily components having a melting point of lower than ordinary temperatures are treated as liquid oils, and those having a melting point of not lower than ordinary temperatures are treated as solid or semisolid oils.

Examples of a slightly water-soluble substances in the oily component are vitamins such as ubiquinone and vitamin P; bactericides such as chlorhexdin hydrochloride, trichlorocarbanilide and Imegassan DP 300; medicines such as dexamethazone acetate; ultraviolet absorbers such as paraaminobenzoic acid (hereinunder referred to as "PABA") and N,N-dimethyl PABA octyl ester; and preservatives such as parahydroxybenzoate.

A mixed dispersion of the above-described essential materials is treated with a strong shear force by an emulsifier having a stronger shear force than a homomixer, thereby improving the transparency, the safety and the stability. As examples of such an emulsifier will be cited Mantongaulin, French press, colloid mill, microfluidizer and ultrasonic emulsifier.

When using a high-pressure homogenizer such as Mantongaulin, a French press or a microfluidizer, emulsification is carried out at a pressure of not less than 1000 psi, more preferably not less than 3000 psi.

In the present invention, the total amount of mixed dispersion may be emulsified. It is also possible to emulsify part of the mixed dispersion and dilute the emulsion with water or another component such as a polyvalent alcohol, as occasion demands. Emulsification is preferably conducted at a temperature not lower than the transition temperature of the gel which is formed by the surfactant and the amphiphile together with water in the system.

The emulsion composition of the present invention may contain other components. For example, ethylene glycol, propylene glycol, 1,3-butylene glycol, dipropylene glycol, glycerol, polyglycerine such as diglycerine, triglycerine and tetraglycerine glucose, maltose, maltitol, sucrose, fructose, xylitol, inositol, pentaerythritol, sorbitol, maltotriose, amylolysis sugar and amylolysis sugar reduced alcohol are usable as a water-phase component. The water phase here is exemplified by an aqueous solution of at least one selected from the group consisting of: water-soluble active substances such as vitamins, e.g., vitamin B, vitamin C and derivatives thereof, pantothenic acid and derivatives thereof and biotin; buffers such as sodium glutamate, alginine, aspattic acid, citric acid, tartaric acid and lactic acid; chelates such as EDTA; ultraviolet absorbers; and various pigments.

The above and other objects, features and advantages of the present invention will become clear from the following description of the preferred embodiments thereof, taken in conjunction with the accompanying drawings.

BRIEF DESCRIPTION OF THE DRAWINGS

FIG. 1 is a schematic view of a general oil-in-water type emulsion composition in the emulsified state;

FIG. 2 is an explanatory view of the factor of the deterioration of the emulsion stability of a general oil-in-water type emulsion composition;

DESCRIPTION OF THE PREFERRED EMBODIMENTS

Figure 3:
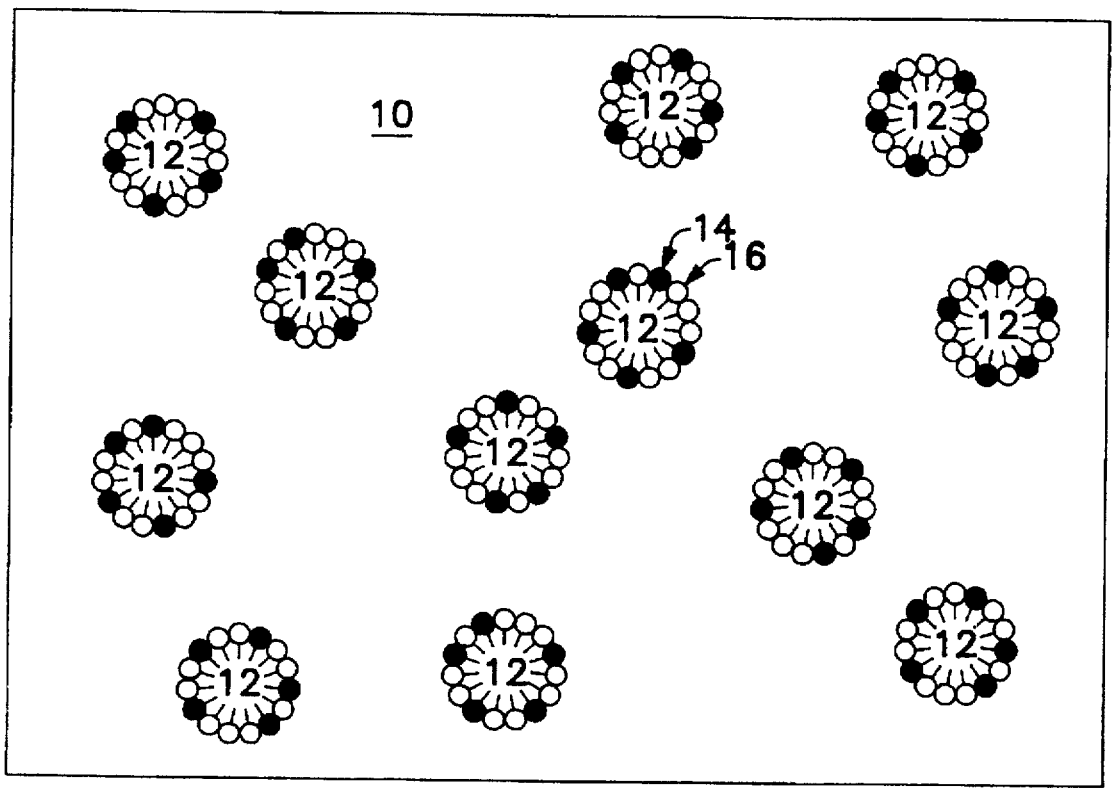
FIG. 3 is an explanatory view of an oil-in-water type emulsion composition according to the present invention in the emulsified state.

The present invention will be explained hereinunder in more detail with reference to preferred embodiments of the present invention. It is to be understood, however, that the present invention is not restricted thereto.

Amount of amphiphile and surfactant existent on the surfaces of the emulsion particles As described above, the amount of surfactant and amphiphile on the surfaces of the emulsion particles and the amount thereof remaining in the water phase exert a great influence on the physical properties of the emulsion composition during preservation and the creamy feel thereof at the time of application to the skin.

Therefore, the present inventors first produced oil-in-water type emulsion compositions in Comparative Examples 1, 2 and 3, and Example 1. Then physical properties of the products were examined, such as the change thereof with time and the feel of the products when they were applied to the skin.

The amount of surfactant and amphiphile on the surfaces of the emulsion particles can be estimated from a change in the area of the peak of the gel transition.

The transition temperature was measured by a differential scanning calorimeter (DSC), DSC 120 (produced by Seiko Instruments Ltd.), and the temperature at the peak of heat absorption observed from the DSC temperature rise curve was regarded as the transition temperature. Experiments were conducted using the components listed in Table 1 below.

TABLE 1

|  | Comp. 1 | Comp. 2 | Comp. 3 | Ex. 1 |
|---|---|---|---|---|
| 1) Behenyl alcohol (%) | 1.0 | 1.0 | 1.0 | 1.0 |
| 2) Stearyl alcohol (%) | 0.5 | 0.5 | 0.5 | 0.5 |
| 3) Behenic acid (%) | 0.5 | 0.5 | 0.5 | 0.5 |
| 4) Stearic acid (%) | 0.5 | 0.5 | 0.5 | 0.5 |
| 5) Liquid paraffin (%) | — | 5.0 | 5.0 | 5.0 |
| 6) KOH (%) | 0.15 | 0.15 | 0.15 | 0.15 |
| 7) 1,3-butylene glycol (%) | 10.0 | 10.0 | 10.0 | 10.0 |
| 8) Ion-exchanged water (%) | 15.0 | 15.0 | 15.0 | 15.0 |
| 9) Ion-exchanged water (%) | Balance | Balance | Balance | Balance |

(Process)

Comparative Example 1: The components (1) to (4) (Table 1) were mixed and stirred at 80° C. The mixture of the components (6) to (9) was heated and dissolved at 70° C. The mixture of the components (1) to (4) was mixed under stirring with the mixture of the components (6) to (9), and emulsified at 80° C. by a homomixer.

Comparative Examples 2 and 3, and Example 1: The components (1) to (5) were mixed and stirred at 80° C. The mixture of the components (6) to (9) was heated and disolved at 70° C. The mixture of the components (1) to (4) was mixed under stirring with the mixture of the components (6) to (9). In Comparative Example 2, after the resultant mixture was emulsified at 80° C. by a homomixer, the component (9) was mixed with the emulsion under stirring. In Comparative Example 3, after the resultant mixture was emulsified at 80° C. under a pressure of 500 psi by a high-pressure homogenizer, the component (9) was mixed with the emulsion under stirring. In Example 1, after the resultant mixture was emulsified at 80° C. under a pressure of 700 psi by a high-pressure homogenizer, the component (9) was mixed with the emulsion under stirring. In this manner, samples having different average emulsion particle diameters were obtained.

Figure 4:
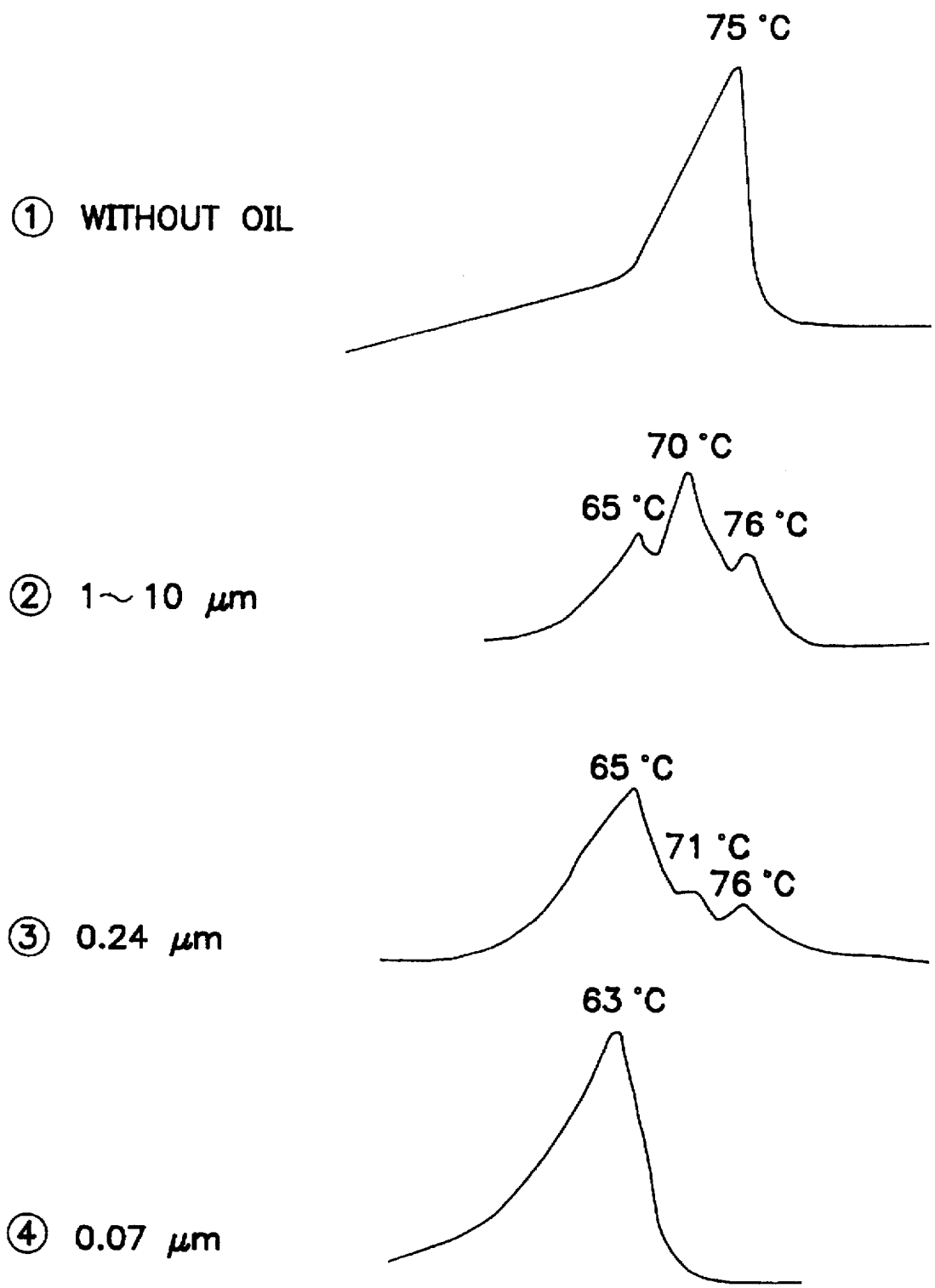
FIG. 4 is an explanatory view of the DSC temperature rise curve of an oil-in-water type emulsion composition according to the present invention.

FIG. 4 shows a change in the DSC curve obtained in heating scans with a change in average emulsion particle diameter. In FIG. 4, the curve (1) represents the transition curve of the sample in Comparative Example 1 in which the system did not contain any oily component. On the curve (1), a single transition peak was observed at 75° C. Since no emulsion is formed in the system which does not contain an oily component, the amphiphile and the surfactant formed a gel in the water phase, and the curve (1) represents this state. In Comparative Examples 2 and 3 and Example 1, the system contained the oily component, and the average emulsion particle diameters were 1 to 10 μm, 0.24 μm and 0.07 μm, respectively. With the reduction in the average emulsion particle diameter, the peaks on the high-temperature side are reduced on the DSC curves and in Example 1, only one peak was observed at the lowest temperature in all the peaks. This suggests that the amphiphile and the surfactant which constitute the gel in the water phase transfer to the interfaces in the emulsion with expansion in the area of the boundary surface of each emulsion particle in the process of reducing the particle size diameters and that the amount of amphiphile and surfactant in the water phase is reduced.

The average emulsion particle diameter was measured through a microscope when the particle diameter was not less than 1 μm. When the particle diameter was less than 1 μm, the average emulsion particle diameter was measured by a dynamic light scattering method using NICOMP-270 (produced by HIAC/ROYCO).

On the DSC curve (4) of Example 1 in which the average emulsion particle diameter was 0.07 μm, a single transition peak was observed at 63° C. This indicates that almost all of amphiphile and the surfactant transferred to the interfaces in the emulsion. The fact that the ratio of the peak on the high-temperature side increases with an increase in particle diameter indicates an increase in the amount of gel component in the water phase, namely, an increase in the amount of amphiphile and surfactant in the water phase. From the point of view of the external appearance of the emulsion composition being close to that of an aqueous solution, and the assurance of the stability of the composition as an article of commerce, it is desirable that the DSC curve has only one peak on the low-temperature side. However, the area of the peaks on the high-temperature side can be about 10% of the total peak area.

The emulsion compositions produced in this manner in Comparative Examples 1, 2 and 3 and Example 1 had the following physical properties. The feel of these compositions thereof, at the time of use were also evaluated and the results are shown in Table 2.

TABLE 2

|  | Comp. 1 | Comp. 2 | Comp. 3 | Ex. 1 |
|---|---|---|---|---|
| Average emulsion particle diameter (μm) | — | 1 to 10 | 0.24 | 0.07 |
| Viscosity (immediately after production) (cps) | 55 | 220 | 25 | 12 |
| External appearance | Cloudy | Cloudy | Slightly Cloudy | Translucent |
| Stability (left at 40° C. for 1 month) | — | o | Δ (Increased turbidity creaming) | o |
| Creamy feel at the time of the application | — | o | o | o |

As is clear from Table 2, although the emulsion composition in Comparative Example 2 produced a creamy feel, the viscosity was so high that the composition did not have physical properties close to those of an aqueous solution. The emulsion composition in Comparative Example 3 had a high transparency and a low viscosity. In other words, it had physical properties close to those of an aqueous solution, but since the amphiphile and the surfactant remained in the water phase, the stability was lowered (generation of blobs, increase in the turbidity, generation of creaming, etc.).

In contrast, in Example 1, not only did the emulsion composition have a high transparency and a low viscosity, but it also had a good stability, and an excellent creamy feel.

Average emulsion particle diameter

The present inventors then investigated the relationship between average emulsion particle diameter, stability, and external appearance of the emulsion composition.

When the average emulsion particle diameter of the oil phase, (which corresponds to the inner phase of the emulsion composition of the present invention), is large, there is a danger that the physical properties will not be close to those of an aqueous solution. In such a case, the stability (generation of creaming, etc. due to the increase in the turbidity) may decrease and the viscosity increase.

The present inventors produced an oil-in-water type emulsion composition which is suitable as an external preparation in accordance with the following prescription. The composition was emulsified by a Mantongaulin while varying the shear force so as to obtain average emulsion particle diameters shown in Table 3 below.

| | |
|---|---|
| (1) Behenyl alcohol | 1.0 |
| (2) Stearyl alcohol | 0.5 |
| (3) Behenic acid | 0.5 |
| (4) Stearic acid | 0.5 |
| (5) Liquid paraffin | 5.0 |
| (6) Potassium hydroxide | 0.15 |
| (7) 1,3-butylene glycol | 10.0 |
| (8) Ion-exchanged water | 10.0 |
| (9) Ion-exchanged water | balance |

(Process)

The components (1) to (5) were mixed and stirred at 80° C. The mixture of the components (6) to (8) was heated and dissolved at 80° C. The mixture of the components (1) to (5) was mixed under stirring with the mixture of the components (6) to (8), and emulsified at 80° C. by the high-pressure homogenizer while varying pressure. Thereafter, the component (9) was mixed with the resultant emulsion under stirring. In this manner, samples were obtained having different average emulsion particle diameters.

In the prescription, behenic acid, stearic acid and potassium hydroxide form fatty acid soap, which functions as a surfactant. The behenic acid and stearic acid which have not been neutralized, behenyl alcohol and stearyl alcohol function as amphiphiles. Table 3 shows the results of the investigation.

TABLE 3

| Average emulsion particle diameter (μ) | Viscosity (cps) | Stability | External appearance |
|---|---|---|---|
| 0.05 | 13.5 | ○ | Translucent |
| 0.06 | 13.5 | ○ | Translucent |
| 0.09 | 14.5 | ○ | Translucent |
| 0.11 | 13.0 | ○ | Translucent |
| 0.14 | 15.2 | ○ | Slightly cloudy |
| 0.17 | 17.1 | Δ | Slightly cloudy |
| 0.20 | 18.5 | Δ | Cloudy |
| 1 to 5 | 37.0 | X | Cloudy |

The stability was visually evaluated after each sample was left for one month.

As is clear from Table 3, both the stability and external appearance were very good when the average emulsion particle diameter was less than about 0.1 μm When the average emulsion particle diameter reached about 0.15 μm, although there was no problem in the stability, the whiteness degree of the external appearance became slightly strong.

When the average emulsion particle diameter exceeded 0.15 μm, the stability was lowered (creaming was produced), and the emulsion composition was apt to become cloudy.

Accordingly, it is to be understood that the suitable average emulsion particle diameter of the emulsion composition of the present invention is not more than 0.15 μm, preferably not more than 0.10 μm.

The ratio of the total amount of amphiphile and surfactant to the amount of oil

The present inventors then investigated the ratio of the total amount of amphiphile and surfactant to the amount of oil.

As described above, it is necessary to transfer substantially the total amount of amphiphile and surfactant to the boundary surfaces of the emulsion particles in the emulsion composition of the present invention.

There is a limit to the reduction in the emulsion particle size, and if the amount of oil mixed with the other components is small, the area of the boundary surface of each emulsion particle becomes relatively small. It is therefore difficult to sufficiently transfer the amphiphile and the surfactant to the boundary surfaces. As a result, the gel components remain in the water phase, and there is a danger of greatly lowering the stability of the emulsion composition.

The present inventors produced oil-in-water type emulsion compositions, each of which is suitable as an external preparation in accordance with the following prescription so as to examine the emulsion particle diameters and the emulsion stability over a period of time.

TABLE 4

| | | | | | | | |
|---|---|---|---|---|---|---|---|
| 1) | Behenyl alcohol (%) | 1.0 | 1.0 | 1.0 | 1.0 | 1.0 | 1.0 |
| 2) | Stearyl alcohol (%) | 0.5 | 0.5 | 0.5 | 0.5 | 0.5 | 0.5 |
| 3) | Behenyl trimethyl ammonium chloride (%) | 1.0 | 1.0 | 1.0 | 1.0 | 1.0 | 1.0 |
| 4) | Liquid paraffin (%) | 1.0 | 1.25 | 2.5 | 5 | 10 | 20 |
| 5) | 1,3-butylene glycol (%) | 15.0 | 15.0 | 15.0 | 15.0 | 15.0 | 15.0 |
| 6) | Ion-exchanged water (%) | 15.0 | 15.0 | 15.0 | 15.0 | 15.0 | 15.0 |
| 7) | Ion-exchanged water (%) | Balance | Balance | Balance | Balance | Balance | Balance |
| | Average emulsion particle diameter | 0.020 | 0.023 | 0.025 | 0.035 | 0.070 | 0.140 |
| | Stability with time | X | ○ | ○ | ○ | ○ | ○ |

(Process)

The components (1), (2) and (4) were mixed and stirred at 80° C. The mixture of the components (3), (5) and (6) was heated and dissolved at 80° C. The mixture of the components (1), (2) and (4) was mixed under stirring of the components (3), (5) and (6), and emulsified at 80° C. by a high-pressure homogenizer under a pressure of 5000 psi. Thereafter, the component (7) was mixed with the resultant emulsion under stirring, thereby obtaining samples.

As is clear from Table 4, when the amount of liquid paraffin as the oil phase was varied between 2.0 to 10.0% with respect to the total amount (2.5%) of amphiphile and surfactant, the smaller the amount of liquid paraffin, the smaller the average emulsion particle diameter. However, the emulsion stability over time was lowered when the amount of liquid paraffin Was 1.0%. This suggests that the ratio of the total amount of amphiphile and surfactant to the amount of oil phase in the present invention should be not less than 1/0.5, more preferably not less than 1/1.

The present inventors also produced samples in accordance with the following prescription so as to investigate the relationship between the total amount of amphiphile and surfactant, and the creamy feel of the product at the time of use.

TABLE 5

| | | | | | |
|---|---|---|---|---|---|
| 1) | Behenyl alcohol (%) | 1.0 | 0.2 | 0.08 | 0.06 |
| 2) | Stearyl alcohol (%) | 0.5 | 0.1 | 0.04 | 0.03 |
| 3) | Behenyl-trimethyl ammonium chloride (%) | 1.0 | 0.2 | 0.03 | 0.06 |
| 4) | liquid paraffin (%) | 4.0 | 4.0 | 4.0 | 4.0 |
| 5) | Vaseline (%) | 1.0 | 1.0 | 1.0 | 1.0 |
| 6) | 1,3-butylene glycol (%) | 15.0 | 15.0 | 15.0 | 15.0 |
| 7) | Ion-exchanged water (%) | 15.0 | 15.0 | 15.0 | 15.0 |
| 8) | Ion-exchanged water | Balance | Balance | Balance | Balance |
| | Creamy feel at the time of application | ◎ | ◎ | ○ | X |

◎: Creamy feel
○: Slightly creamy feel
Δ: Scarcely any creamy feel
X: No creamy feel (Process)

The components (1), (2), (4) and (5) were mixed and stirred at 70° C. The mixture of the components (3), (6) and (7) was heated and dissolved at 70° C. The mixure of the components (1), (2), (4) and (5) was mixed under stirring with the mixture of the components (3), (6) and (7), and emulsified at 70° C. by a high-pressure homogenizer under a preessure of 5000 psi. Thereafter, the component (8) was mixed with the resultant emulsion under stirring, thereby obtaining samples.

As is clear from Table 5, when the total amount of amphiphile and surfactant was varied between 2.5 to 0.15% with respect to the amount (5%) of oil phase, the smaller the total amount of amphiphile and surfactant, the more the loss of the creamy feel of the emulsion composition at the time of application. This suggests that the total amount of amphiphile and surfactant should be not less than 0.2%, preferably not less than 0.5% of the amount of oil phase in the present invention.

Composition of the amphiphile and surfactant

The present inventors next investigated the composition of the amphiphile and the surfactant used in the present invention.

It is necessary that the amphiphile and the surfactant used in the present invention form a gel in a surfactant-amphiphatic substance-water system at least in a temperature range of the solidification point of water phase to ordinary temperatures. The transition temperature of the gel is preferably not lower than 60° C.

The transition temperature of the gel formed in a surfactant-amphiphile-water system is generally a temperature 10° to 20° C. higher than the temperature at which no gel is formed (the system begins to flow). It is considered that when the transition temperature of a gel is not lower than 60° C., the gel is formed at normal temperatures.

The present inventors produced oil-in-water type emulsion compositions each having the following basic composition while varying the combination of the surfactant and the amphiphile, and the change in the physical properties were examined.

| Emulsion composition | (%) |
|---|---|
| (1) Liquid paraffin | 5.0 |
| (2) Surfactant | 1.0 |

| | (%) |
|---|---|
| (3) Amphiphile | 1.5 |
| (4) 1,3-butylene glycol | 10.0 |
| (5) Ion-exchanged water | 20.0 |
| (6) Ion-exchanged water | balance |
| Gel | |
| (1) Surfactant | 1.0 |
| (2) Amphiphile | 1.5 |
| (3) Ion-exchanged water | balance |

(Process)

Emulsion composition: The components (1) and (3) were mixed and stirred at 70° to 80° C. The mixture of the components (2), (4) and (5) was heated and dissolved at 80° C. The mixture of the components (1) and (3) was mixed under stirring with the mixture of the components (2), (4) and (5) so as to emulsify the resultant mixture. The emulsion was further emulsified at 70° to 80° C. by a high-pressure homogenizer under a pressure of 7000 psi. Thereafter, the component (6) was mixed with the resultant emulsion under stirring, thereby obtaining samples. Gel: The component (2) was stirred at 80° C. The mixture of the components (1) and (3) was heated and dissolved at 80° C. The component (2) was mixed under stirring with the mixture of the components (1) and (3) and treated by a homomixer.

The results are shown in Tables 6 to 8.

In each of Tables 6 to 8, when there are two types of surfactant or amphiphile, the mixing ratio thereof was 1:1.

Each emulsion was left at 40° C. and at 50° C. for 1 month and the stability thereof was evaluated.

○: Good

▲: Increase in the turbidity or generation of agglomerates

X: Solidification

TABLE 6

| Surfactant | Sodium cetyl sulfate | Sodium lauryl sulfate | Behenyl-trimethyl ammonium chloride | Stearyl-trimethyl ammonium chloride |
|---|---|---|---|---|
| Amphiphatic substance | Behenyl alcohol Stearyl alcohol | Behenyl alcohol | Behenyl alcohol | Behenyl alcohol |
| Transition temperature of gel | 75° C. | 68° C. | 79° C. | 77° C. |
| Stability of emulsion composition | | | | |
| (40° C., 1 month) | ○ | ○ | ○ | ○ |
| (5° C., 1 month) | ○ | ○ | ○ | ○ |

TABLE 7

| Surfactant | POE (15) Oleyl ether | Potassium behenate Potassium stearate | Potassium stearate | Potassium stearate |
|---|---|---|---|---|
| Amphiphatic substance | Cetyl alcohol Stearyl alcohol | Behenyl alcohol Stearyl alcohol | Behenyl alcohol Stearyl alcohol | Behenyl alcohol Stearyl alcohol |

TABLE 7-continued

| | 57° C. | 78° C. | 73° C. | 67° C. |
|---|---|---|---|---|
| Transition temperature of gel | | | | |
| Stability | | | | |
| (40° C., 1 month) | X | ○ | ○ | Δ |
| (5° C., 1 month) | Δ | ○ | ○ | ○ |

TABLE 8

| | | | |
|---|---|---|---|
| Surfactant | Potassium stearate Potassium palmitate | Potassium behenate | Potassium stearate |
| Amphiphatic substance | Cetyl alcohol Stearyl alcohol | Stearyl alcohol | Cetyl alcohol |
| Transition temperature of gel | 64° C. | 69° C. | 64° C. |
| Stability | | | |
| (40° C., 1 month) | Δ | Δ | X |
| (5° C., 1 month) | ○ | ○ | Δ |

As is clear from each of Tables 6 to 8, when combination of a surfactant and an amphiphile which forms a gel have a high transition temperature, the stability of the emulsion composition is good. In addition, when the combination of a surfactant and an amphiphile which have different carbon chain lengths are used, the stability is very good.

Preferred embodiments of an emulsion composition according to the present invention will now be explained.

| Embodiment 1 Skin Lotion | (%) |
|---|---|
| (1) Behenyl alcohol | 2.0 |
| (2) Behenic acid | 1.5 |
| (3) Liquid paraffin | 7.0 |
| (4) Vitamin E acetate | 0.5 |
| (5) Butyl parahydroxybenzoate | 0.2 |
| (6) KOH | 0.15 |
| (7) Ethanol | 5.0 |
| (8) Glycerol | 5.0 |
| (9) Perfume | 0.05 |
| (10) Ion-exchanged water | 15.0 |
| (11) Trisodium edetate | 0.01 |
| (12) Sodium 2-hydroxy-4-methocy-benzophenone-5-sulfonate | 0.05 |
| (13) Ion-exchanged water | balance |

The components (1) to (5) were mixed and stirred at 70° C. The mixture of the components (6) to (10) was heated and dissolved at 70° C. The mixture of the components (1) to (5) was mixed under stirring with the mixture of the components (6) to (10) so as to emulsify the resultant mixture. The emulsion was further emulsified at 75° C. by a high-pressure homogenizer under a pressure of 6000 psi. Thereafter, the mixture of the components (11) to (13) was mixed with the resultant emulsion under stirring, thereby obtaining a translucent skin lotion having a low viscosity. The average emulsion particle diameter of the skin lotion which was measured by a dynamic light scattering method was 0.05 μm, and the viscosity thereof was 10 cps. When it was spread over the skin, it had a creamy feel.

| Embodiment 2 Whitening Skin Lotion | (%) |
|---|---|
| (1) Behenyl alcohol | 1.5 |
| (2) Behenic acid | 1.0 |
| (3) Liquid paraffin | 5.0 |
| (4) Vitamin E acetate | 0.5 |
| (5) Butyl parahydroxybenzoate | 0.2 |
| (6) KOH | 0.13 |
| (7) 1,3-butylene glycol | 7.0 |
| (8) Glycerol | 8.0 |
| (9) Perfume | 0.05 |
| (10) Ion-exchanged water | 15.0 |
| (11) Arbutin | 3.0 |
| (12) Ion-exchanged water | balance |

The components (1) to (5) were mixed and stirred at 70° C. The mixture of the components (6) to (10) was heated and dissolved at 70° C. The mixture of the components (1) to (5) was mixed under stirring with the mixture of the components (6) to (10) so as to emulsify the resultant mixture. The emulsion was further emulsified at 75° C. by a high-pressure homogenizer under a pressure of 8000 psi. Thereafter, the mixture of the components (11) and (12) was mixed with the resultant emulsion under stirring, thereby obtaining a translucent skin lotion having a low viscosity.

The average emulsion particle diameter of the skin lotion was 0.04 μm, and the viscosity thereof was 10 cps. When it was actually spread over the skin, it had a creamy feel.

| Embodiment 3 Skin Lotion | (%) |
|---|---|
| (1) Behenyl alcohol | 2.0 |
| (2) Stearyl alcohol | 1.5 |
| (3) Behenic acid | 1.0 |
| (4) Stearic acid | 1.0 |
| (5) Liquid paraffin | 8.0 |
| (6) Vaseline | 2.0 |
| (7) Vitamin E acetate | 0.5 |
| (8) Butyl parahydroxybenzoate | 0.2 |
| (9) KOH | 0.2 |
| (10) 1,3-butylene glycol | 7.0 |
| (11) Glycerol | 10.0 |
| (12) Perfume | 0.05 |
| (13) Ion-exchanged water | 40.0 |
| (14) Ion-exchanged water | balance |

The components (1) to (8) were mixed and stirred at 70° C. The mixture of the components (9) to (13) was heated and dissolved at 70° C. The mixture of the components (1) to (8) was mixed under stirring with the mixture of the components (9) to (13) so as to emulsify the resultant mixture. The emulsion was further emulsified at 80° C. by a high-pressure homogenizer under a pressure of 4000 psi. Thereafter, the component (14) was mixed with the resultant emulsion under stirring, thereby obtaining a translucent skin lotion having a low viscosity.

The average emulsion particle diameter of the skin lotion which was measured by a dynamic light scattering method was 0.07 μm, and the viscosity thereof was 25 cps. When it was spread over the skin, it had a creamy feel.

| Embodiment 4 Hair Lotion | (%) |
|---|---|
| (1) Behenyl alcohol | 1.5 |
| (2) Stearyl alcohol | 0.3 |
| (3) Dimethyl silicone (20 cps) | 10.0 |
| (4) Behenyltrimethyl ammonium chloride | 1.0 |
| (5) 1,3-butylene glycol | 5.0 |
| (6) Glycerol | 10.0 |

-continued

| Embodiment 4 Hair Lotion | (%) |
| --- | --- |
| (7) Perfume | 0.05 |
| (8) Methylparahydroxybenzoate | 0.2 |
| (9) Ion-exchanged water | balance |

The components (1) to (3) were mixed and stirred at 70° C. The mixture of the components (4) to (9) was heated and dissolved at 70° C. The mixture of the components (1) to (3) was mixed under stirring with the mixture of the components (4) to (9) so as to emulsify the resultant mixture. The emulsion was further emulsified at 75° C. by a high-pressure homogenizer under a pressure of 8000 psi, thereby obtaining a transparent hair lotion having a low viscosity.

The average emulsion particle diameter of the hair lotion which was measured by a dynamic light scattering method was 0.12 μm, and the viscosity thereof was 20 cps. When it was actually spread over the hair, it had a creamy feel.

| Embodiment 5 Sunscreening Lotion | (%) |
| --- | --- |
| (1) Behenyl alcohol | 1.0 |
| (2) Stearyl alcohol | 0.5 |
| (3) Behenic acid | 0.5 |
| (4) Stearic acid | 0.5 |
| (5) Neopentyl glycol dicaprate | 5.0 |
| (6) Glycerylmono-2-ethylhexanoyl diparamethoxycinnamate | 1.0 |
| (7) Butylparahydroxybenzoate | 0.2 |
| (8) KOH | 0.2 |
| (9) 1,3-butylene glycol | 7.0 |
| (10) Glycerol | 8.0 |
| (11) Perfume | 0.05 |
| (12) Ion-exchanged water | 15.0 |
| (13) Ion-exchanged water | balance |

The components (1) to (7) were mixed and stirred at 70° C. The mixture of the components (8) to (12) was heated and dissolved at 70° C. The mixture of the components (1) to (7) was mixed under stirring with the mixture of the components (8) to (12) so as to emulsify the resultant mixture. The emulsion was further emulsified at 70° C. by a high-pressure homogenizer under a pressure of 6000 psi. Thereafter, the component (13) was mixed with the resultant emulsion under stirring, thereby obtaining a translucent sunscreening lotion having a low viscosity. The average emulsion particle diameter of the skin lotion which was measured by a dynamic light scattering method was 0.05 μm, and the viscosity thereof was 15 cps. When it was spread over the skin, it had a creamy feel.

As described above, an oil-in-water type emulsion composition according to the present invention has a comparatively high transparency and a low viscosity. In other words, it has physical properties close to those of an aqueous solution in the preserved state. On the other and, at the time of application, it has a creamy feel.

That is, an oil-in-water type emulsion composition having substantially the total amount of amphiphile and surfactant on the interface between each oil phase and a water phase can have not only physical properties close to those of an aqueous solution but also a creamy feel at the time of use.

While there has been described what are at present considered to be preferred embodiments of the invention, it will be understood that various modifications may be made thereto, and it is intended that the appended claims cover all such modifications which fall within the true spirit and scope of the invention.

What is claimed is:

1. An oil-in-water type emulsion composition comprising:
   an amphiphile and a surfactant wherein said surfactant is one or more substances which are capable of forming a gel in an amphiphile-surfactant-water system at a temperature of not lower than ordinary temperatures;
   oil; and
   water;
   wherein not less than 90% by an area ratio according to DSC of said amphiphile and surfactant exist on boundary surfaces of emulsion particles; said amphiphile and surfactant are capable of forming a gel having a transition temperature of not lower than about 60° C. in said amphiphile-surfactant-water system; an average emulsion particle diameter is not more than 0.15 μm; the amount of said oil is not less than ½ of the total amount of said amphiphile and surfactant; the total amount of said amphiphile and surfactant is not less than 0.2 wt. % of a water phase; said amphiphile is a higher alcohol and/or a higher fatty acid having a carbon chain length of not less than 16; and said surfactant is cationic or anionic.

2. The oil-in-water type emulsion composition of claim 1, wherein amphiphile is a higher fatty alcohol.

3. The oil-in-water type emulsion composition of claim 1, wherein the viscosity of the composition is equal to or less than 25 cps.

4. The oil-in-water type emulsion composition of claim 1, wherein the composition is translucent or slightly cloudy.

5. The oil-in-water type emulsion composition of claim 1, wherein the viscosity of the composition is equal to or less than 25 cps, and the composition is translucent or slightly cloudy.

* * * * *